United States Patent
Lopatin et al.

(10) Patent No.: US 10,591,443 B2
(45) Date of Patent: Mar. 17, 2020

(54) APPARATUS FOR DETERMINING OR MONITORING A PROCESS VARIABLE OF AUTOMATION TECHNOLOGY

(71) Applicant: Endress + Hauser GmbH + Co. KG, Maulburg (DE)

(72) Inventors: Sergej Lopatin, Lorrach (DE); Raphael Kuhnen, Ebringen (DE); Dietmar Fruhauf, Lorrach (DE)

(73) Assignee: ENDRESS+HAUSER SE+CO. KG, Maulburg (DE)

( * ) Notice: Subject to any disclaimer, the term of this patent is extended or adjusted under 35 U.S.C. 154(b) by 127 days.

(21) Appl. No.: 14/913,418

(22) PCT Filed: Jul. 8, 2014

(86) PCT No.: PCT/EP2014/064593
§ 371 (c)(1),
(2) Date: Feb. 22, 2016

(87) PCT Pub. No.: WO2015/028179
PCT Pub. Date: Mar. 5, 2015

(65) Prior Publication Data
US 2016/0209368 A1   Jul. 21, 2016

(30) Foreign Application Priority Data
Aug. 28, 2013   (DE) .......... 10 2013 109 331

(51) Int. Cl.
*G01N 29/036*   (2006.01)
*G01N 11/16*   (2006.01)
(Continued)

(52) U.S. Cl.
CPC ....... *G01N 29/036* (2013.01); *G01F 23/2966* (2013.01); *G01F 23/2967* (2013.01);
(Continued)

(58) Field of Classification Search
CPC ........ G01N 29/036; G01N 9/002; G01N 9/24; G01N 11/16; G01F 23/2966; G01F 23/2967
(Continued)

(56) References Cited

U.S. PATENT DOCUMENTS

| 4,770,038 A | 9/1988 | Zuckerwar et al. |
| 6,079,266 A * | 6/2000 | Wright ................ G01F 23/2966 73/290 B |

(Continued)

FOREIGN PATENT DOCUMENTS

| DE | 3207305 A1 | 9/1983 |
| DE | 4327167 A1 | 2/1995 |

(Continued)

OTHER PUBLICATIONS

English Translation of International Preliminary Report on Patentability, WIPO, Geneva, dated Mar. 10, 2016.
(Continued)

*Primary Examiner* — Tarun Sinha
(74) *Attorney, Agent, or Firm* — Bacon & Thomas, PLLC

(57) ABSTRACT

A vibration sensor comprising an oscillatable unit, which is composed of a membrane with an inner surface and an outer surface and, in given cases, at least one oscillatory element secured on the outer surface of the membrane. A transmitting/receiving unit is provided, which with a predetermined exciter frequency excites the oscillatable unit to execute oscillations and which receives oscillations of the oscillatable unit. A control/evaluation unit is provided, which signals reaching of the predetermined fill level or ascertains the density, respectively the viscosity, of the medium. In order to be able to apply the vibration sensor in high temperature applications, a disc shaped element of a magnetostrictive material is provided, which has a force trans- (Continued)

mitting connection with the inner surface of the membrane. The transmitting/receiving unit is an electromagnetic drive.

13 Claims, 4 Drawing Sheets

(51) Int. Cl.
G01F 23/296 (2006.01)
G01N 9/00 (2006.01)
G01N 9/24 (2006.01)

(52) U.S. Cl.
CPC ............... *G01N 9/002* (2013.01); *G01N 9/24* (2013.01); *G01N 11/16* (2013.01); *G01N 2009/006* (2013.01); *G01N 2291/014* (2013.01); *G01N 2291/021* (2013.01); *G01N 2291/022* (2013.01)

(58) Field of Classification Search
USPC .......................................................... 73/579
See application file for complete search history.

(56) References Cited

U.S. PATENT DOCUMENTS 6,539,806 B2   4/2003   Wright
7,598,820 B2   10/2009  Alvarez et al.
2002/0124645 A1*  9/2002  Wright .................... G01F 23/18
                                                      73/290 V
2006/0230841 A1   10/2006  Shrikrishna
2007/0186646 A1*  8/2007   Frick .................... G01F 23/0076
                                                      73/290 V
2013/0322200 A1*  12/2013  Ludwig .................. G01N 1/286
                                                      366/108
2015/0047428 A1*  2/2015   Lopatin ............... G01F 25/0061
                                                      73/290 V

FOREIGN PATENT DOCUMENTS

DE   102010030332 A1   12/2011
EP       1239267 A2    9/2002
GB       2263976 A     8/1993
WO      2011039266 A1  4/2011

OTHER PUBLICATIONS

International Search Report, EPO, The Netherlands, dated Sep. 11, 2014.
German Search Report, German PTO, Munich, dated Mar. 26, 2014.

* cited by examiner

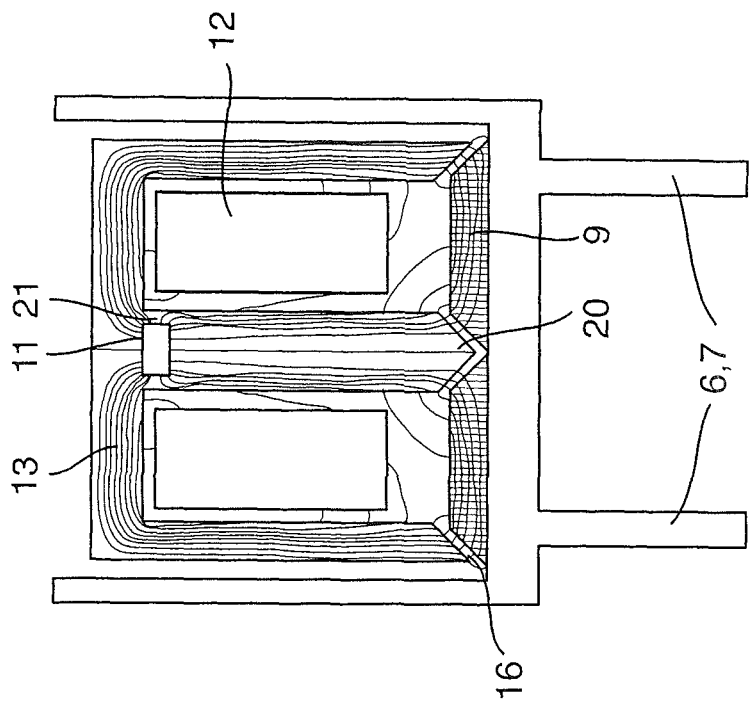
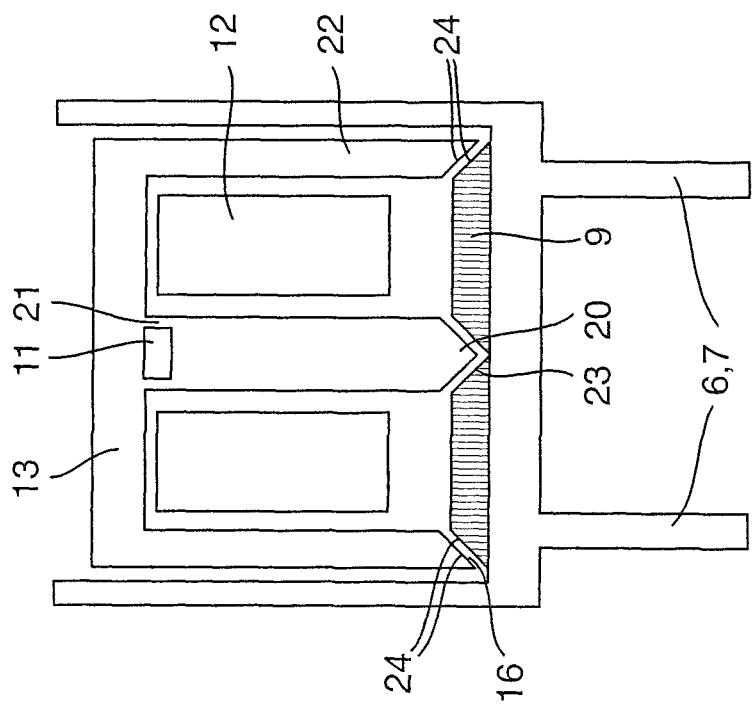

APPARATUS FOR DETERMINING OR MONITORING A PROCESS VARIABLE OF AUTOMATION TECHNOLOGY

TECHNICAL FIELD

The invention relates to an apparatus for determining or monitoring a process variable, especially a predetermined fill level (limit-level), the density or the viscosity of a medium in a container. The apparatus comprises an oscillatable unit, which is placed at the height of the predetermined fill level or which is so placed in the container that it extends to a defined immersion depth in the medium, wherein a transmitting/receiving unit is provided, which with a predetermined exciter frequency excites the oscillatable unit to execute oscillations and which receives oscillations of the oscillatable unit, and wherein a control/evaluation unit is provided, which signals reaching of the predetermined fill level or ascertains the density, respectively the viscosity, of the medium. Such sensors are also referred to as vibration sensors or vibronic sensors.

BACKGROUND DISCUSSION

The oscillatable unit can be differently embodied, depending on application: as an oscillatory fork having two fork tines arranged symmetrically on a membrane (FIG. 1a), as a single rod, in the case of which only one tine is arranged centrally on a membrane (FIG. 1b) or as a membrane alone (FIG. 1c). Vibration sensors with oscillatory forks are applied in liquids, gases and solids and are manufactured and sold by the applicant under the mark LIQUIPHANT. Known under the mark SOLIPHANT are vibration sensors with a single rod. These are designated mainly for use in solids. Known from German Patent DE 10 2005 044 725 A1, moreover, is an embodiment of a membrane oscillator, which is suitable for use in the most varied of media.

Vibronic sensors oscillate at a defined resonant frequency so that they execute a harmonic oscillation. The resonant frequency is determined by the construction of the sensor and the materials used. Oscillations can be characterized by frequency and damping. If the oscillatable unit oscillates in a liquid medium with a high density, the density of the medium, as a coupled, moved mass, has an influence on the oscillatable unit. As a result, the oscillation frequency in a liquid medium is lower than in a gaseous medium. A frequency change indicates, thus, for example, a transition from a gaseous state to a liquid state of a medium. Furthermore damping by the medium has an influence on the oscillations of a vibronic sensor. Bulk goods such as wheat or rice damp the oscillations of the oscillatable unit of a vibration sensor and bring about a drastic amplitude decrease at the transition air/bulk good.

Vibration sensors embodied as limit level measuring devices, thus, utilize the effect that both the oscillation frequency as well as also the oscillation amplitude depend on the respective degree of coverage of the oscillatory element: While the oscillatory element can in air execute its oscillations freely and without damping, it experiences frequency and amplitude changes, as soon as it becomes immersed partially or completely in the medium. Based on a predetermined frequency change (usually frequency is measured), it can be clear that a predetermined fill level of the medium in the container has been reached. The frequency change in non-damping media such as gases and low viscosity liquids depends on the density of the medium. The frequency change is sufficient to detect the medium and to evaluate its density. Fill level measuring devices are used, moreover, principally as overfill preventers or for the purpose of protection against a pump running empty.

As already indicated, the damping of the oscillation of the oscillatable unit is predominantly determined by the frictional forces of the solid particles or molecules of the respective medium. Therefore, in the case of constant degree of coverage, there is a functional relationship between oscillation amplitude and density of a bulk good (the friction in heavy bulk goods with a high bulk good density is higher than in the case of lighter bulk goods) or between the oscillation amplitude and viscosity, so that vibration sensors are suitable both for fill level measurements as well as also for density determination in bulk goods. Furthermore, vibronic sensors are applied for determining the viscosity of a liquid medium.

The oscillations of a vibration sensor are produced by an electromechanical transducer. The electromechanical transducer is usually a piezo drive having at least one piezoelectric element. The piezo drive excites in the vibration sensor harmonic oscillations of a resonant frequency and compensates for energy losses, which occur in the oscillatable unit. Piezo drives can achieve a high efficiency. Since the energy supply is relatively small, wide application in automation technology is possible. Further information can be found, for example, in German Patent DE 10 2008 050 266 A1. Often so-called stack drives are applied as piezo drives. In the case of stack drives, a number of disk-shaped piezoelectric elements are arranged stacked on top of one another. Moreover, bimorph drives are used for oscillation production and oscillation detection. In principle, a bimorph drive is composed of a disk shaped piezoelectric element connected with the membrane by a force transmitting connection, wherein the piezoelectric element has opposite polarization in at least two areas. European patents EP 0 985 916 A1 and EP 1 281 051 B1 describe different embodiments of bimorph drives.

In the case of fill level determination, the evaluation unit monitors the oscillation frequency and/or the oscillation amplitude of the oscillatory element and signals the states 'sensor covered', respectively 'sensor uncovered', as soon as the measurement signals subceed or exceed a predetermined reference value. A corresponding report to operating personnel can occur by optical and/or acoustical means. Alternatively or supplementally, a switching event is triggered; thus, for instance, a supply or drain valve on the container is opened or closed.

Piezo technology based on LZT (lead zirconate titanate) piezoceramic materials is best suitable for use at temperatures up to 300° C. There are piezoceramic materials, which keep their piezoelectric properties at temperatures above 300° C. These have, however, the disadvantage that they are markedly less effective than the LZT-based materials. Such high temperature materials are little suitable for use in vibration sensors.

The main impediment for application of piezoceramic materials in vibration sensors at temperatures above 300° C. is the great difference in the thermal coefficients of expansion of metals and ceramic materials. The piezoceramic elements act as force providers in vibration drives: Therefore, the piezoelectric, respectively piezoceramic, elements must be connected by a force transmitting connection with the membrane, which is usually manufactured of stainless steel. Due to the different thermal coefficients of expansion, mechanical stresses in the piezoceramic elements get so high with rising temperature that the piezoceramic elements eventually fracture—the result is a total failure of the vibration sensor.

In order to avoid these problems, Published International Applications WO 2007/113011 and WO 2007/114950 A1 describe vibration sensors, which use a special electromagnetic drive. Essential components of the electromagnetic drive are a coil and a permanent magnet. If the electromagnetic drive is supplied with an alternating voltage signal, then an alternating magnetic field is produced. As a result of the alternating magnetic field, a periodic force acts on the oscillatable unit of the vibration sensor and excites it to execute oscillations. In the case of this known sensor, the changing of electrical energy into mechanical energy occurs via a magnetic field. In the case of an electromagnetic drive, the differences of the thermal coefficients of expansion of the materials in the sensor are of lesser significance. Since in contrast to the piezoelectric drives a force transmitting connection between two completely different materials, such as e.g. the stainless steel membrane and the piezoceramic, does not need to be used, a vibration sensor with an electromagnetic drive is also applicable in a higher and broader temperature range, especially temperatures between −200° C. and 450-500° C.

A disadvantage in the case of the known vibration sensors with electromagnetic drive is that a permanent magnet interacting with a coil as force provider has a clearly lesser efficiency than a piezo drive. While the electromagnetic drive develops relatively high forces in the region of the membrane, nevertheless the deflection of the oscillatory fork as a result of the non-force transmitting connection between membrane and drive is small. As a result thereof, a vibration sensor with electromagnetic drive requires more energy in comparison to a vibration sensor with piezo drive. This makes its use in explosion-endangered regions problematic.

U.S. Pat. No. 3,256,738 discloses a magnetostrictive sensor for detecting the limit level of a medium in a container. The sensor housing is also in this case sealed on its underside with a membrane. A tubular component of a magnetostrictive material extends into the housing interior and is welded in one of its end regions with the central region of the membrane. Force transmission can occur through the weld. The second end region of the tubular component is free. Located in the outer region of the tubular magnetostrictive component as transmitting/receiving unit are two coils with an annular permanent magnet lying therebetween. In the case of the known solution, small tubes of magnetostrictive material are excited to execute longitudinal resonant oscillations. Longitudinally oscillating resonators have a high mechanical quality and react with an amplitude change, as soon as they come in contact with the medium to be monitored. The known sensor is excited to execute resonant oscillations by changing the tube length in a harmonic magnetic field.

A disadvantage of the known magnetostrictive sensor is that it is not mechanically decoupled from the container wall. Depending on connection, there is the danger that it will stop working. For exciting oscillations in applicant's vibration sensors, which are applied as safety switches, the known magnetostrictive drive is not suitable.

SUMMARY OF THE INVENTION

An object of the invention is to provide a vibration sensor for use in the high temperature region. The terminology, high temperature region, means in connection with the invention especially the region above 300° C.

The object is achieved by features including that a disc shaped element of a magnetostrictive material is provided, which is connected with the inner surface of the membrane by force transmitting connection. The disk shaped element of the magnetostrictive material can have a circular, annular or rectangular shape. The transmitting/receiving unit is an electromagnetic drive, which—as already mentioned above—is suitable without problem for use in the high temperature region.

Magnetostrictive materials are typically metal alloys, which are magnetic, especially ferromagnetic. In the case of applying a magnetic field, they elastically change length. This effect is also referred to as joule-magnetostriction.

A great advantage of magnetostrictive materials is that they can be connected without problem by a force transmitting connection with the metal membrane of a vibration sensor. For example, the force transmitting connection can occur via a solder. Soldered joints can provide excellent force transfer, depending on applied solder, up to temperatures in the range 700-900° C. Of course, it is also possible to implement the force transmitting connection via a (e.g. laser-) welding- or adhesion process. As a result, it is possible to use the vibration sensor of the invention at temperatures above 300° C.

Due to the force transmitting connection (areal or e.g. only in the outer region of the disk shaped magnetostrictive material) between the disk shaped magnetostrictive material and the membrane, force transfer is excellent. Therefore, the efficiency of the electromagnetic exciting of the mechanical oscillation is very high. As a result, the vibration sensor of the invention requires comparatively little energy, so that it also can be suitable for use in explosion-endangered regions of automation technology.

A further advantage of the vibration sensor of the invention is its compact and cost effective construction.

Examples of magnetostrictive materials, which can be used in connection with the solution of the invention, include pure nickel (Ni) with a Curie temperature of 358° C., cobalt (Co) with a Curie temperature of 1120° C., terbium-iron (TbFe2), which is applicable up to 424° C., or an alloy referred to as Terfenol-D, which maintains its magnetostrictive property up to 380° C. These magnetostrictive materials have different magnetostrictive coefficients. Preferably in connection with the invention, materials are applied, which have besides a sufficiently high magnetostriction also a high Curie temperature. For applications up to 400° C., e.g. a combination of high temperature stainless steel and cobalt or TbFe2 can be used. Best suitable for soldering is a hard metal compound, especially a standard e.g. nickel-based solder with a soldering temperature of about 950° C.

In an advantageous embodiment of the vibration sensor of the invention, the electromagnetic drive is a modularly embodied unit, which is secured in the interior of the housing. Any type of securement can be used. The force transmitting connection of the drive with the membrane, which is indispensable in the case of a piezoelectric drive, is absent.

The electromagnetic drive is composed of at least one coil, at least one coil core reinforcing the magnetic field of the coil and at least one permanent magnet. The permanent magnet is preferably annularly embodied and arranged in the outer region of the coil. The electromagnetic drive is so arranged within the housing that a gap is formed between the disk shaped element of magnetostrictive material and the corresponding end region of the electromagnetic drive. Preferably, the gap has a thickness of 0.1-1 mm.

An advantageous embodiment of the vibration sensor of the invention provides that the magnetic field strength in the case of application of a permanent magnet is so selected that it lies in a region, in which the relative expansion, respectively the relative length, respectively diameter, change, of the magnetostrictive material of the disk shaped element has as a function of the magnetic field strength of the electromagnetic drive a high or maximum slope. Premagnetization by means of the permanent magnet can define the optimal working point of the vibration sensor.

In an advantageous embodiment, no permanent magnet is needed. In this case, a magnetostrictive material is selected, whose magnetostriction curve in the region of the zero-point already has a sufficiently high slope that the alternating magnetic field of the electromagnetic drive is suitable for producing the exciter frequency.

Moreover, an advantageous embodiment of the vibration sensor of the invention provides that the adjoining end regions of coil core and disk shaped magnetostrictive element are so embodied that the magnetic field lines in the interior of the coil core and disk shaped magnetostrictive element are essentially planparallel, and, in the case of cylindrical symmetry, extend radially. In this way, the efficiency can be optimized. Additionally or alternatively, the disk shaped magnetostrictive material is a laminate of single plies. In this way, the occurrence of eddy currents is effectively counteracted.

BRIEF DESCRIPTION OF THE DRAWINGS

The invention will now be explained in greater detail based on the appended drawing, the figures of which show as follows:

FIG. 4a is a longitudinal section of an embodiment of the vibration sensor of the invention; and FIG. 4b is a longitudinal section of an embodiment of the vibration sensor of the invention with optimized magnetization geometry.

DETAILED DESCRIPTION IN CONJUNCTION WITH THE DRAWINGS

Figure 1A:
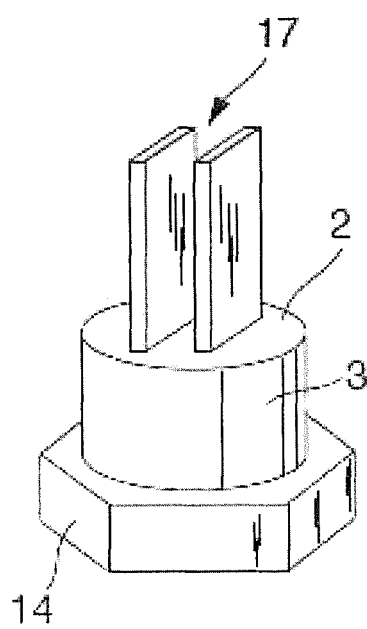
FIG. 1a is a schematic representation of a vibration sensor known from the state of the art with an oscillatory fork.
Figure 1B:
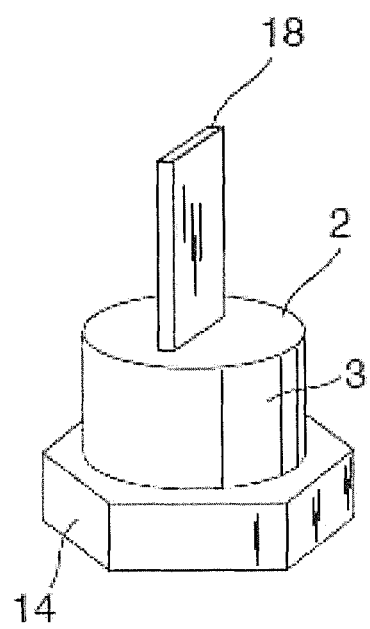
FIG. 1b is a schematic representation of a vibration sensor known from the state of the art with a single rod.
Figure 1C:
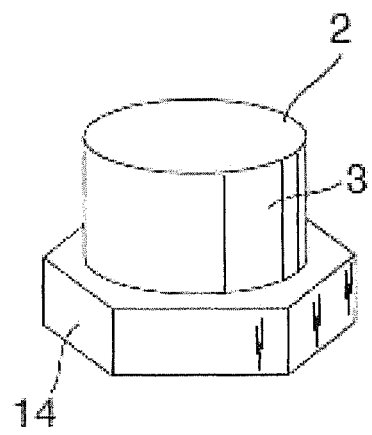
FIG. 1c is a schematic representation of a vibration sensor known from the state of the art and embodied as a membrane oscillator.

Schematically shown in FIGS. 1a, 1b and 1c are oscillatable units 2 of vibration sensors 1 known from the state of the art. In the case of FIG. 1a, the oscillatable unit 2 is composed of a membrane 3 and an oscillatory fork 17. In the case of FIG. 1b, a single rod 18 is secured on the membrane 3. FIG. 1c shows a membrane oscillator, in the case of which the oscillatable unit 2 is formed by the membrane 3 alone.

Figure 2:
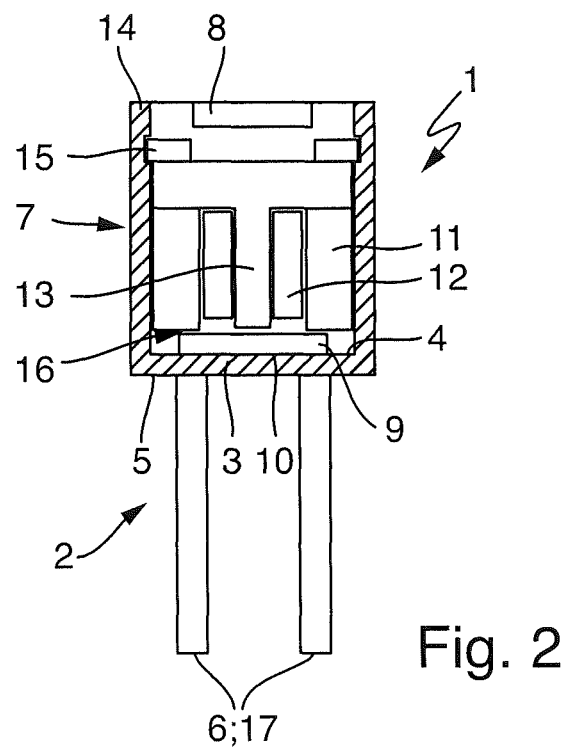
FIG. 2 is a longitudinal section of an embodiment of the vibration sensor of the invention in schematic representation.

FIG. 2 shows a longitudinal section of an embodiment of the vibration sensor 1 of the invention with a magnetostrictive bimorph element 19 in schematic representation. Bimorph element 19 is composed of an essentially disk shaped element 9 of a magnetostrictive metal material, which is coupled with the membrane 3 via a force transmitting connection 10, especially a solder-, weld- or adhesive connection. Bimorph element 19 closes the tubular sensor housing 14 on one of its two end regions. Arranged in the sensor housing 14 above the disk shaped element 9, respectively above the bimorph element 19, is an electromagnetic drive 7. The electromagnetic drive 7 is composed in the illustrated case of a coil 12 with a coil core 13 and a permanent magnet 11 arranged around coil 12. Permanent magnet 11 is preferably annularly embodied. Of course, permanent magnet 11 can also be a washer shaped ring magnet.

Coil core 13 is manufactured of a ferromagnetic alloy. Preferably, it is so embodied that formation of eddy currents is reduced to a minimum. Preferably, electromagnetic drive 7 is constructed as a modular unit. Via a preferably metal securement element 15, the electromagnetic drive 7 is secured in the sensor housing 14. Securement element 15 is, for example, one or more screws or a retaining ring. Of course, it is also possible to secure the electromagnetic drive 7 in the sensor housing 14 via a welding or soldering process.

The disk shaped element 9 of a magnetostrictive material is separated from the permanent magnet 11 and especially the ferromagnetic coil core 13 by a gap 16. Preferably, the thickness of the gap 16 lies in the range between 0.1 and 1.0 mm. A force transmitting connection of the drive, such as required in the case of a piezoelectric drive, is absent in the case of the solution of the invention.

Coil 12 is fed via the control/evaluation unit 8 with a periodic, respectively harmonic, electrical excitation current. In this way, there arises in association with the constant magnetic field strength $H_0$ of the permanent magnet 11 a harmonic magnetic field $H=H_0+\Delta H$. Via this periodically changing magnetic field H, the bimorph element 19 and, thus, also the oscillatable unit 2 are excited to execute harmonic oscillations.

The harmonic magnetic field of field strength $\Delta H$ causes the disk shaped element 9 to undergo a periodic change of diameter $\Delta D$ with the frequency of the excitation frequency. Since the disk shaped element 9 of magnetostrictive material is coupled by force transmitting connection with membrane 3 of the vibration-sensors 1, a periodic diameter, respectively length, change leads to a harmonic bending oscillation of the bimorph element 19. Controlled by the exciter current of the coil 12, the vibration sensor 1 is, thus, excited to execute oscillations with a desired oscillation frequency, especially with a resonant frequency.

Figure 3:
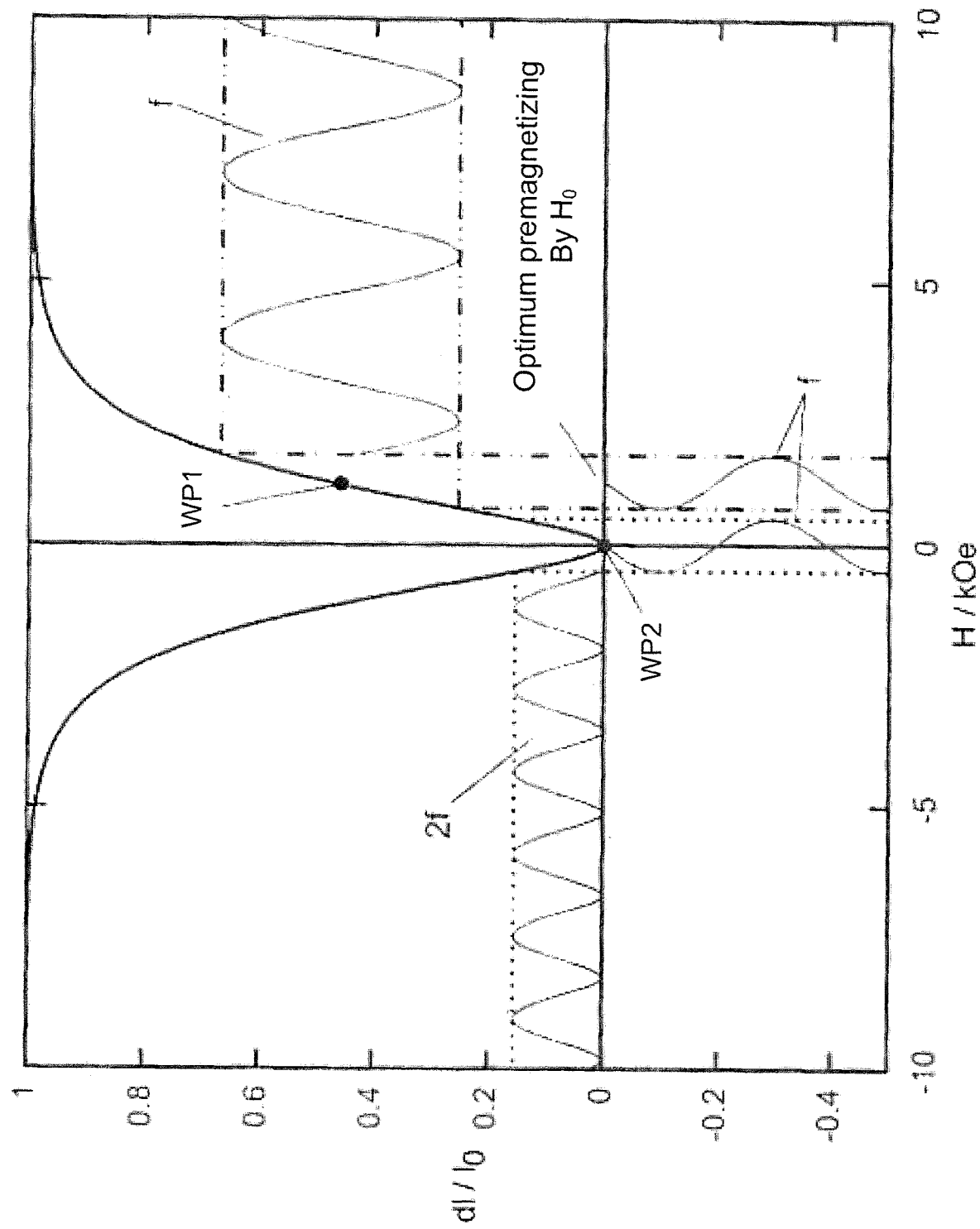
FIG. 3 is a graph showing longitudinal extension of a magnetostrictive material as a function of magnetic field strength.

The driving magnetic field H is composed in the shown case of the magnetic field $H_0$ of the permanent magnet 11 and the alternating magnetic field, respectively the harmonic magnetic field, $\Delta H$ of the coil 12. In such case, $\Delta H$ is the amplitude of the alternating magnetic field, which is modulated onto the constant magnetic field $H_0$ of the permanent magnet 11. Via the magnetic field $H_0$ of the permanent magnet 11, it is achieved—such as shown in FIG. 3—that the vibration sensor of the invention works about the working point WP1. The working point WP1 is preferably located in a region, in which the alternating magnetic field $\Delta H$ effects as large as possible length—, respectively diameter, change of the magnetostrictive material of the disk shaped element 9. The change of the diameter, respectively the length change $\Delta l$, of the magnetostrictive material of the disk shaped element 9 in the region of a low magnetic field strength H can be mathematically described approximately by a parabola. The corresponding formula becomes:

$$\frac{\Delta l}{l_0} = \gamma \cdot H^2,$$

In such case, $$\frac{\Delta l}{l_0}$$

is the relative expansion of the magnetostrictive material in the case of the acting harmonic magnetic field, and γ is a coefficient, which correlates with the magnetostrictive constant λ. The above formula can be rewritten in the following way:

$$\frac{\Delta l}{l_0} = \gamma \cdot H^2 = \gamma \cdot (H_0 + \Delta H)^2 = \gamma \cdot (H_0^2 + 2\Delta H \cdot H_0 + \Delta H^2).$$

The term $\gamma \cdot H_0^2$ is a constant, which is independent of the magnetic field strength of the harmonic magnetic field with the amplitude ΔH. It corresponds to the pre-deformation of the bimorph element 19. This pre-deformation is present as a result of the magnetic field strength $H_0$ of the magnetic field of the permanent magnet 11. The term $\gamma \cdot \Delta H^2$ is negligible. Relevant for the excitation is the term $\gamma \cdot 2\Delta H \cdot H_0$, which shows that a maximum slope of the expansion $$\frac{\Delta l}{l_0}$$

as a function of field strength ΔH of the harmonic magnetic field in the case of usual magnetostrictive materials make sense only in combination with the defined field strength of a permanent magnet 11. The magnetic field strength $H_0$ of the permanent magnet 11 is specific for each magnetostrictive material and should preferably lie at the maximum slope or in the region of the maximum slope of the expansion curve, respectively magnetostriction curve, illustrated in FIG. 3. For the expansion curve shown in FIG. 3, the optimal premagnetization due to the magnetic field strength $H_0$ of the permanent magnet 11 lies in the range between 1 and 2 kOe.

The magnetic field strength $H_0$ of the permanent magnet 11 must not be so great that the field strength H of the magnetic field of the electromagnetic drive 7 lies in the region of saturation. Since in this region the slope of the expansion curve is very small, the oscillation of the oscillatable unit 3 would be correspondingly small. Saturation in the case of the embodiment shown in FIG. 3 occurs at a magnetic field strength H of about 5 kOe.

The exciting of an oscillatable unit 2 with a magnetostrictive bimorph element 19 is suitable for use in the case of all vibration sensors 1, especially also for the vibration sensors 1 shown in FIGS. 1a, 1b and 1c. A decisive advantage of the combination of bimorph- and electromagnetic drive is that the vibration sensor 1 of the invention is also best suitable for applications in the high temperature region. The field of use of the vibration sensor of the invention is lastly only limited by the Curie temperature of the material of the permanent magnet 11, the Curie temperature of the material of the magnetostrictive element 9 and the temperature tolerance of the material of the coil 12. Typically, the solution of the invention can, however, be operated with the mentioned cost effective and available materials at least in the temperature range of 400-500° C. The temperature range can be expanded to higher temperatures, when a higher cost level for materials, which can still be used at higher temperatures, can be tolerated.

Figure 2A:
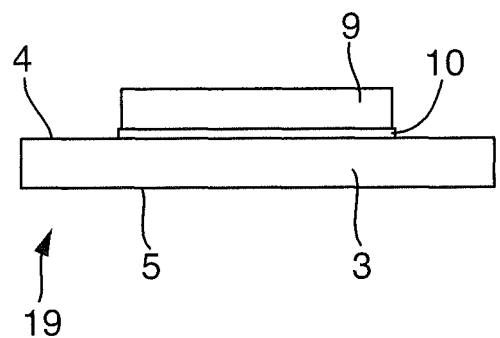
FIG. 2a is an enlarged representation of the membrane with applied magnetostrictive element of FIG. 2.
Figure 2B:
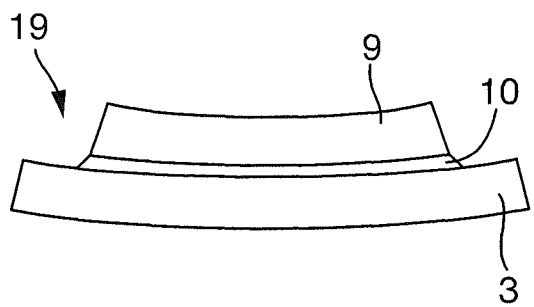
FIG. 2b is the membrane shown in FIG. 2a with applied magnetostrictive element in the case of supply of an electromagnetic field.

As evident from FIGS. 2a and 2b, the layer structure of the invention (=bimorph element 19) composed of a metal membrane 3 and a disk shaped element 9 of a magnetostrictive alloy can be optimally used in a bimorph element 19 for producing and receiving oscillations of the oscillatable unit 2. The membrane 3 and the disk shaped magnetostrictive element 9 are preferably embodied as thin platelets. The force transmitting connection 10 in the bimorph element 19 is achieved, for example, via a solder layer of a hard metal alloy. As already mentioned above, a force transmitting connection 10 for use in the high temperature region can also be implemented via a welding or adhesion process.

The solutions shown in FIGS. 2 and 4 utilize a permanent magnet 11, in order to bring the working point WP1 of the vibration sensor 1 of the invention into the region, in which the length, respectively diameter, change of the disk shaped magnetostrictive element 9 is as great as possible. Preferably aimed for is an optimal premagnetization $H_0$ dependent on the respectively used magnetostrictive material. Subsequently correspondingly pronounced is the oscillation amplitude of the vibration sensor 1 excited by the alternating magnetic field ΔH.

FIG. 3 shows supplementally the case, in which no permanent magnet 11 is used. In the case of such a solution, the working point WP2 of the vibration sensor 1 lies in the zero-point of the magnetostriction curve. Preferably used for the disk shaped element 9, in this case, is a magnetostrictive material, such as, for example, an alloy referred to as Galfenol, which has a relatively large length, respectively diameter, change in the region of the zero-point. If a corresponding material is used, then the alternating magnetic field ΔH effects a symmetric oscillation around the zero-point. As shown in FIG. 3, the length, respectively the diameter, of the magnetostrictive material of the disk shaped element 9 changes with a frequency, which is twice that of the exciter frequency of the alternating magnetic field ΔH. While an embodiment of the vibration sensor 1 of the invention with permanent magnet 11 can implement a higher oscillation amplitude, the variant without permanent magnet 11 has the advantage that a lower exciter frequency can be used. In this way, the skin effect can be reduced, which is always greater at higher frequencies. Therefore, the solution without permanent magnet 11 is—energetically considered—very advantageous.

FIGS. 4a and 4b show a longitudinal section through an embodiment of the vibration sensor 1 of the invention optimized for uniform magnetizing. In order to achieve an as uniform as possible magnetizing over the entire volume of the magnetostrictive element 9, the permanent magnet 11 is so embodied (e.g. as small circular disk), such that it can be inserted in the central coil core 13. The position in the coil core 13 can, in such case, be freely selected. Alternatively, an option is to embody the permanent magnet 11 as a ring magnet and integrate such in the outer coil core 22. Furthermore, an option is, instead of the permanent magnet 11, to use an additional, second coil, or to operate the coil 12 with a superimposed DC-electrical current.

Coil core 13 is composed of a material with high magnetic permeability and includes a cone 20 in the region facing the magnetostrictive element 9. The disk shaped magnetostrictive element 9 is so embodied that it has in the central region, corresponding to the cone 20, a recess 23, into which the cone 20 protrudes. The edge regions of the disk shaped magnetostrictive element 9 and the end regions of the outer coil core 22 likewise have corresponding chamfers 24. Cone 20 and chamfers 24 serve for targeted guiding of the magnetic field lines in the disk shaped magnetostrictive element 9 into and out of the disk shaped magnetostrictive element 9, so that the field lines within the material extend in high measure planparallelly, and radially in the case of cylindrical symmetry. Coil core 13 includes in the region around the permanent magnet 11 a bridge region 21, which likewise serves for optimal guiding of the magnetic field produced by the coil 12.

The disk shaped magnetostrictive element 9 is manufactured, for example, from a solid piece of material. In order to prevent eddy currents and the deformation of the magnetic field H resulting therefrom, the disk shaped magnetostrictive element 9 is preferably composed of laminated layers. The lamination can occur by an areal adhesive connecting or by a solder, weld or adhesive connecting on the edges of the individual lamella.

The outer coil core 22 serves, furthermore, for magnetic shielding from external fields.

Since the magnetic field $H_0$ of the permanent magnet 11 is conveyed in the same coil core 13 as the magnetic field $\Delta H$ of the coil 12, the two magnetic fields $H_0$, $\Delta H$ in the magnetostrictive material of the disk shaped element 9 are oriented optimally planparallelly, in the case of cylindrical symmetry radially, to one another, which leads to a marked increasing of the efficiency.

As already described above in connection with FIG. 3, the permanent magnet 11 can be omitted, when the exciter coil 12 is operated bipolarly at the half resonant frequency. Since the magnetostriction curve (FIG. 3) is symmetric relative to H, at each zero crossing the coil current achieves a minimum deflection, whereby an excitation is generated at doubled frequency. This method enables halving the exciter frequency and, thus, a strong reduction of the arising eddy currents and the losses associated therewith. An alternative or additional reduction of the exciter frequency can be achieved by so optimizing the oscillatory elements, e.g. the fork tines, that they are suitable for operation with harmonic waves.

The invention claimed is:

1. Apparatus for determining or monitoring a process variable, especially a predetermined fill level, density or viscosity of a medium in a container, comprising:
    a housing and an oscillatable unit, which oscillatable unit has a membrane with an inner surface and an outer surface and, in given cases, at least one oscillatory element secured on said outer surface of said membrane and which apparatus is placed at the height of the predetermined fill level or which is so placed in the container that it extends to a defined immersion depth in the medium;
    a transmitting/receiving unit, which with a predetermined exciter frequency excites said oscillatable unit to execute oscillations and which receives oscillations of said oscillatable unit;
    a control/evaluation unit, which signals reaching of the predetermined fill level or ascertains the density, respectively the viscosity, of the medium; and
    a disc shaped bimorph element of a magnetostrictive material, which has an area force transmitting connection with said inner surface of said membrane, wherein:
said transmitting/receiving unit is an electromagnetic drive comprising a coil, and a coil core; and
said electromagnetic drive is so arranged within the housing that a gap is provided between said disc shaped element of magnetostrictive material and the corresponding end region of said electromagnetic drive.

2. The apparatus as claimed in claim 1, wherein:
said disc shaped element of magnetostrictive material is embodied with circular or rectangular shape.

3. The apparatus as claimed in claim 1, wherein:
said force transmitting connection is a soldering, a welding or an adhesion.

4. The apparatus as claimed in claim 1, wherein:
the material of said disc shaped magnetostrictive element is nickel, cobalt, terbium-iron, an alloy referred to as Terfenol-D or an alloy as referred to Galfenol.

5. The apparatus as claimed in claim 1, wherein:
said force transmitting connection is implemented via a solder, especially a standard solder based on nickel or silver.

6. The apparatus as claimed in claim 1, wherein:
said force transmitting connection is implemented via a welding process or via an adhesion process.

7. The apparatus as claimed in claim 1, wherein:
said electromagnetic drive is a modularly embodied unit, which is secured in the interior of said housing by means of a securement means.

8. The apparatus as claimed in claim 1, wherein:
said electromagnetic drive comprises a permanent magnet.

9. The apparatus as claimed in claim 1, wherein:
said electromagnetic drive is so arranged within said housing that said gap has preferably a thickness of 0.1-1 mm.

10. The apparatus as claimed in claim 8, wherein:
the magnetic field strength in the case of application of said permanent magnet is so selected that it lies in a region, in which the relative expansion, respectively the relative length, respectively diameter, change of said magnetostrictive material of said disc shaped element has as a function of the magnetic field strength of said electromagnetic drive a high or maximum slope.

11. The apparatus as claimed in claim 8, wherein:
in case said permanent magnet is not present, the magnetostrictive material of said disc shaped element is so formed that the magnetostriction curve has in the region of the zero-point a high slope suitable for producing the exciter frequency.

12. The apparatus as claimed in claim 8, wherein:
adjoining regions of said coil core and said disk shaped magnetostrictive element are so embodied that magnetic field lines in the interior of said coil core and said disc shaped magnetostrictive element extend essentially plan parallel, and radially in the case of cylindrical symmetry.

13. The apparatus as claimed in claim 1, wherein:
said oscillatable unit is one of: an oscillatory fork, a single rod and a membrane.

* * * * *